United States Patent
Brück et al.

(10) Patent No.: US 8,282,798 B2
(45) Date of Patent: Oct. 9, 2012

(54) GAS PROBE WITH HYGROSCOPICALLY COATED PROTECTIVE DEVICE, METHOD OF PRODUCING A GAS PROBE AND EXHAUST GAS PURIFICATION COMPONENT AND VEHICLE HAVING A GAS PROBE

(75) Inventors: Rolf Brück, Bergisch Gladbach (DE); Bernhard Pfalzgraf, Ingolstadt (DE); Bodo Odendall, Neuburg (DE)

(73) Assignees: EMITEC Gesellschaft fuer Emissionstechnologie mbH, Lohmar (DE); Audi AG, Ingolstadt (DE)

( * ) Notice: Subject to any disclaimer, the term of this patent is extended or adjusted under 35 U.S.C. 154(b) by 845 days.

(21) Appl. No.: 11/545,249

(22) Filed: Oct. 10, 2006

(65) Prior Publication Data
US 2007/0068809 A1    Mar. 29, 2007

Related U.S. Application Data

(63) Continuation of application No. PCT/EP2005/003374, filed on Mar. 31, 2005.

(30) Foreign Application Priority Data

Apr. 7, 2004 (DE) .......... 10 2004 017 586

(51) Int. Cl.
*G01N 27/26* (2006.01)
*G01N 31/12* (2006.01)
*G01K 1/08* (2006.01)
*G01N 33/22* (2006.01)

(52) U.S. Cl. ........ 204/428; 204/424; 204/427; 204/431; 422/78; 422/83; 422/94; 205/784; 374/144; 436/127; 436/137

(58) Field of Classification Search .................. None
See application file for complete search history.

(56) References Cited

U.S. PATENT DOCUMENTS

| 4,793,181 | A | 12/1988 | Djorup |
| 5,387,329 | A | 2/1995 | Foos et al. |
| 5,762,771 | A | 6/1998 | Yamada et al. |
| 5,958,200 | A | 9/1999 | Kessel |
| 6,637,254 | B2 | 10/2003 | Wagner et al. |
| 6,699,376 | B2 | 3/2004 | Naito |
| 2002/0134692 | A1* | 9/2002 | Nelson .......... 205/784 |

FOREIGN PATENT DOCUMENTS

| DE | 38 18 736 A1 | 12/1988 |
| DE | 197 17 056 C1 | 5/1998 |
| DE | 100 48 241 C1 | 4/2002 |
| DE | 101 59 858 A1 | 6/2002 |
| JP | 53142296 A | 12/1978 |
| JP | 09222416 A | 8/1997 |
| JP | 11051897 A | 2/1999 |
| JP | 2002174620 A | 6/2002 |

* cited by examiner

*Primary Examiner* — Neil N Turk
(74) *Attorney, Agent, or Firm* — Laurence A. Greenberg; Werner H. Stemer; Ralph E. Locher

(57) ABSTRACT

A gas probe, in particular a lambda probe for the analysis of exhaust gases from a mobile internal combustion engine, includes at least one protective device, at least partly surrounding a sensitive sensor element of the gas probe, which comes into contact with a gas. The at least one protective device includes a gas contact face which at least partly has a hygroscopic surface.

12 Claims, 1 Drawing Sheet

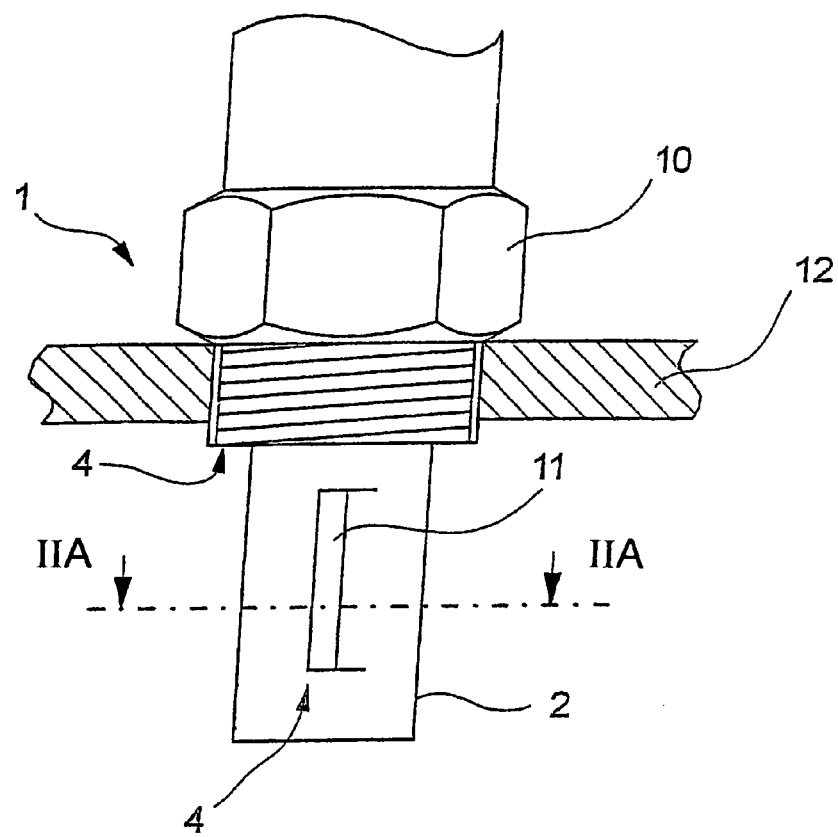
FIG. 1
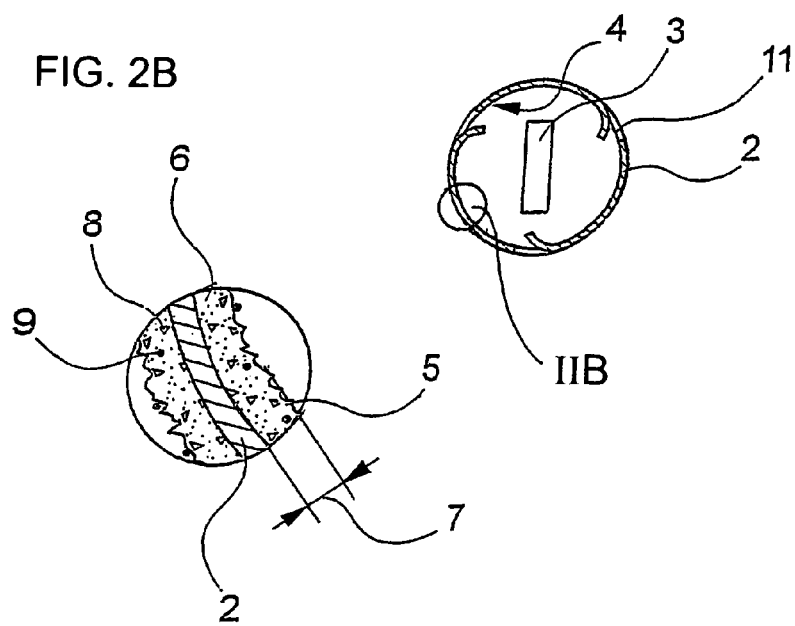
FIG. 2A
FIG. 2B

GAS PROBE WITH HYGROSCOPICALLY COATED PROTECTIVE DEVICE, METHOD OF PRODUCING A GAS PROBE AND EXHAUST GAS PURIFICATION COMPONENT AND VEHICLE HAVING A GAS PROBE

CROSS-REFERENCE TO RELATED APPLICATIONS

This is a continuing application, under 35 U.S.C. §120, of copending International Application No. PCT/EP2005/003374, filed Mar. 31, 2005, which designated the U.S.; this application also claims the priority, under 35 U.S.C. §119, of German Patent Application DE 10 2004 017 586.1, filed Apr. 7, 2004; the prior applications are herewith incorporated by reference in their entirety.

BACKGROUND OF THE INVENTION

Field of the Invention

The invention relates to a gas probe, in particular a lambda probe for analyzing exhaust gases of a mobile internal combustion engine. The invention also relates to a method for producing a gas probe and to an exhaust gas purification component and a vehicle having a gas probe.

Such gas probes conventionally have a sensitive component (sensor element) which can be used to analyze gases, in particular exhaust gases in exhaust systems of internal combustion engines. In order to protect it from damage as a result of mechanical and thermal effects, the sensor element is conventionally surrounded by a protective pipe which allows the gas to be analyzed to pass through suitable openings to the lambda probe sensor element, which is disposed within the protective pipe. The protective pipe primarily serves to avoid transport damage and installation damage and to avoid thermal shock loading of the heated sensitive component of the lambda probe as a result of contact with water droplets which form from water vapor in the gas flow.

Since the gas probe is normally in contact with a hot exhaust gas flow which flows past the gas probe, it could be observed in known gas probes that water vapor in the exhaust gas accumulated on the protective pipe. The water vapor condensed on the surface of the gas probe and formed droplets which endangered the sensor element.

SUMMARY OF THE INVENTION

It is accordingly an object of the invention to provide a gas probe with a hygroscopically coated protective device, a method for producing a gas probe and an exhaust gas purification component and a vehicle having a gas probe, which overcome the here-inafore-mentioned disadvantages of the heretofore-known devices and methods of this general type and in which the gas probe is more reliable than known gas probes despite the fact that the sensor element comes into contact with water droplets. The gas probe should also have a simple structure and should be producible without great expenditure, and cost-effectively, within the context of series production. The known technical problems of the presently available gas probes should also at least be lessened.

With the foregoing and other objects in view there is provided, in accordance with the invention, a gas probe, in particular a lambda probe for analyzing exhaust gases of a mobile internal combustion engine. The gas probe comprises a sensitive component (sensor element) configured to come into contact with a gas. At least one protective device at least regionally surrounds the sensitive sensor element. The at least one protective device includes a gas contact face at least partially having a hygroscopic surface.

On one hand, the at least one protective device—two or three such protective devices (if appropriate, disposed concentrically with respect to one another) can be provided under some circumstances—provides protection against transport damage and/or installation damage, and therefore has a relatively stable construction. The protective device also ensures that the sensor element does not come into contact with impurities (particulates, soot, etc.) in the gas flow and/or with water droplets. At the same time, however, the protective device allows the gas to be analyzed to pass to the sensor element. A protective device of this type is conventionally a type of housing, cap, tube, grille etc., with openings being provided through which the gas can flow-in to internal regions having the sensor element.

It is proposed according to the invention that the protective device, in particular all the protective devices, at least partially have a hygroscopic surface on the faces which come into contact with the gas flow to be analyzed. "Hygroscopic" means in particular that the surface is capable of absorbing water vapor out of the gas flow and/or preventing the formation of water droplets on the gas contact face. For this purpose, the gas contact face itself can be made hygroscopic, for example through the use of a particular construction of the surface roughness and/or of the porosity. It is, however, also possible for the gas contact face to be covered with an additional layer of another material which is different from the material of the protective device.

In accordance with another feature of the invention, it is particularly advantageous for the hygroscopic surface to be formed at least partially with a coating which advantageously includes a desiccant or drying agent that is resistant to high temperatures. Various salts or organic substances, for example, could be used as a desiccant. The coating is advantageously also resistant to water shock and particularly resistant to erosion and corrosion.

In accordance with a further feature of the invention, the gas probe has a coating with a layer thickness in a range of from 10 μm (micrometers) to 50 μm. The layer thickness is preferably 15 μm to 25 μm. It is necessary for the coating on the protective device to be particularly adhesive because of the intense thermal loading, for example in the exhaust system of a motor vehicle. In order to ensure that the coating remains on the protective device permanently, the layer thickness is relatively small so as to avoid flaking.

In accordance with an added feature of the invention, the coating has a porosity which is such that the pore volume per unit volume of the coating is in a range of from 30% to 90%. In other words, this means that, relative to a predefined unit of volume, the volume formed by the pores (averaged statistically) accounts for 30% to 90%, preferably about 50%.

In accordance with an additional feature of the invention, the gas probe includes an oxide coating, and in particular the coating includes at least one of the oxides titanium oxide, zirconium oxide and aluminum oxide. The oxides, which are resistant to high temperature, are favorable with regard to the hygroscopic action of the coating.

In accordance with yet another feature of the invention, in particular if a gas probe of this type is disposed in the exhaust system of a motor vehicle, it is advantageous if the coating has constituents which have a catalytic action, in particular a noble metal (for example platinum, rhodium, etc.). This means that the surface which is in contact with the exhaust gas is simultaneously used to convert pollutants that are contained in the exhaust gas. However, in order to ensure that the composition of the gas flow to be analyzed is not adversely affected to a relevant degree, it is generally also proposed that the coating not have any effect (for example a storage capacity) on those constituents of the gas flow, for example oxygen, which are determined metrologically by the gas probe.

In accordance with yet a further feature of the invention, the further components which come into contact with the gas also at least partially have a hygroscopic surface, particularly a base body of the gas probe. The base body constitutes the receptacle for the sensitive component, and conventionally has a thread at the outer periphery in order to fix the gas probe in a housing. In order to prevent water droplets from forming on the base body, the latter is also provided with a hygroscopic surface. As an alternative or in addition thereto, the hygroscopic surface can be formed through the use of at least one separate shaped body which at least partially covers or encloses the components of interest. The shaped body can be formed so as to be joined to the component or plurality of components in a cohesive and/or form-locking, in particular captively held, fashion. A form-locking connection is one which connects two elements together due to the shape of the elements themselves, as opposed to a force-locking connection, which locks the elements together by force external to the elements.

In accordance with yet an added feature of the invention, with regard to cost-effective production of a gas probe of this type, it is also proposed that the at least one protective device be a cap which includes a material that is resistant to high temperatures and can be deep-drawn. The cap can thus be produced very accurately in high quantities for series production in particular. In this case, a required characteristic of the material which can be deep-drawn is in particular that the latter has a maximum drawing ratio ($\beta_{max}$) in a range of from 1.6 to 2.0. The maximum drawing ratio is determined through the use of a deep-drawing test (for example according to Swift), with cylindrical cups being drawn from circular sheet metal blanks of progressively greater diameter ($d_{0max}$). The diameter is increased in a stepped fashion, while the punch diameter ($d_1$) remains constant. The characteristic value is the maximum drawing ratio, at which the limit of the drawing capability of the metal sheet is reached before the cup base fractures ($\beta_{max} = d_{0max}/d_1$).

In accordance with yet an additional feature of the invention, the gas probe, which includes at least one protective device and a base body, provides at least one oxide-forming surface for the components. This means that the protective device and/or the base body can be at least partially thermally treated in such a way that an oxide, in particular aluminum oxide, forms on its surface. The oxide makes it possible for the subsequent coating to be applied in such a way that it is permanent even if the surface is subjected to high thermal and dynamic loads.

In accordance with again another feature of the invention, an embodiment of a gas probe in which the at least one protective device can be electrically heated, is also advantageous. The heating can, in particular, be carried out for short periods and discontinuously in order to vaporize the water which is retained in the coating. In this case, it is advantageous for this to be carried out in situations in which the exhaust gas is at a relatively low temperature, for example before or directly after the engine is started and in idle phases of the engine.

With the objects of the invention in view, there is also provided a method for producing a gas probe, in particular a lambda probe for analyzing exhaust gases of a mobile internal combustion engine. The method comprises providing a base body and providing a sensitive component (sensor element) for coming into contact with a gas. The sensitive sensor element is at least regionally surrounded by at least one protective device. At least one of the at least one protective device or the base body is at least partially provided with a hygroscopic coating. It is possible in this way to produce, in particular, a gas probe according to the invention as described previously herein.

In this case, if appropriate, free regions are to be provided in particular where the surface is disposed close to other functional faces. Functional faces have a clear function, for example they serve as connecting faces between components, as (electrical) contact faces, as labeling faces, etc. It is thus advantageous, for example, for the base body and/or the protective device to have no coating at those points where they are connected to one another, or to further components of the gas sensor, through the use of a form-locking (crimp) connection and/or a connection produced by joining (welding, brazing, soldering or the like).

In accordance with another mode of the invention, it is particularly advantageous for the surfaces which are to be provided with the coating to be pre-treated, with an oxide being formed on the surface, in particular. An oxide can be formed on the surface through the use of thermal treatment if the material of the at least one protective device or of the base body has corresponding constituents. It is, however, also possible, in an additional production step, for the material to initially be applied to the surface, and for the material to be subsequently alloyed on.

In accordance with a further mode of the invention, under some circumstances, it is advantageous for the at least one protective device or the base body to be aluminized before being coated. This means, for example, that an aluminum wrought alloy is applied to the surface and is fixed to the surface through the use of subsequent thermal treatment. The provision of aluminum makes retrospective formation of aluminum oxide possible. The aluminum oxide is particularly suitable as a substrate layer for the subsequent hygroscopic coating.

In accordance with an added mode of the invention, in this context, it is particularly advantageous for the at least one protective device to be a shaped, in particular deep-drawn part, for which the aluminizing process takes place before the shaping process, and a homogenizing process is advantageously carried out after the shaping step.

In accordance with an additional mode of the invention, the application of the coating includes at least one of the following production steps: spraying, dipping, sputtering, thermal spraying.

In the case of spraying or sputtering, a substrate, for example air, is used when applying the coating to the surface which is to be coated. In the case of dipping, the part which is to be coated is dipped into a bath of the coating. In order to provide a permanent coating, it is advantageous in the three previously mentioned processes for an oxide coating to be formed first. It is possible to dispense with an oxide-forming measure of this type when applying the coating through the use of thermal spraying, since the temperature ranges used therein ensure sufficient cohesion or sufficient adhesive forces between the surface and the coating. During thermal spraying, temperatures of over 500° C., preferably of over 900° C. (plasma spraying), are conventionally used during application. It is possible, if appropriate, to provide smaller layer thicknesses (for example less than 40 μm).

In order to ensure uniform distribution of the coating or a predominantly even layer thickness, further processing steps can be necessary, for example rotation of the part (utilization of centrifugal forces), knocking (utilization of impulse action), blowing (use of a high-pressure gas flow), etc. It is to be ensured in particular that the gas inlet openings and gas outlet openings of the protective device are not closed off to an excessive degree.

With the objects of the invention in view, there is additionally provided an exhaust gas purification component, comprising at least one gas probe according to the invention.

The gas probe is particularly advantageously combined with an exhaust gas purification component. The expression "exhaust gas purification component" is intended to be a generic term for all components which are suitable for exhaust gas aftertreatment, in particular for catalytic converters, flow mixers, filters, adsorbers, hydrocarbon traps or soot traps.

With the objects of the invention in view, there is concomitantly provided a vehicle, comprising an exhaust system including at least one gas probe according to the invention.

A gas probe is particularly advantageously provided in the exhaust gas system of a vehicle, in particular of a motor vehicle.

Other features which are considered as characteristic for the invention are set forth in the appended claims, noting that any technologically expedient combination of the features specified in the claims, if appropriate including features of the description, can lead to advantageous embodiments of the invention.

Although the invention is illustrated and described herein as embodied in a gas probe with a hygroscopically coated protective device, a method for producing a gas probe and an exhaust gas purification component and a vehicle having a gas probe, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a fragmentary, diagrammatic, partially-sectional view of a gas probe;

FIG. 2A is a cross-sectional view of the gas probe which is taken along a line IIA-IIA of FIG. 1, in the direction of the arrows; and FIG. 2B is an enlarged, cross-sectional view of a portion IIB of FIG. 2A.

DESCRIPTION OF THE PREFERRED EMBODIMENTS

Referring now to the figures of the drawings in detail and first, particularly, to FIG. 1 thereof, there is seen a diagrammatic illustration of a structure of a gas probe 1 having a base body 10 and a protective device 2. The gas probe 1 is passed through a housing 12 (for example the housing of an exhaust gas line or an exhaust gas purification component) and is fixed to the latter. In this case, a part of the gas probe 1 which includes the protective device 2 is in contact with a gas flow which is to be analyzed. Both the protective device 2 and the base body 10 have one or more gas contact faces 4, that is to say surfaces which come into contact with the gas which is to be analyzed. In this case, at least at times, the gas flow which is to be analyzed includes water vapor, which can condense on the gas contact faces 4 under some circumstances. A sensor element 3 (shown in FIG. 2A) is disposed in the interior of the protective device 2. Openings 11 in the protective device 2 make it possible for the gas flow which is to be analyzed to come into contact with the sensitive component (sensor element 3).

As is indicated by the section line IIA-IIA in FIG. 1, FIG. 2A shows a cross-section through the protective device 2 of the gas probe 1. In this case, the protective device 2 is illustrated as a substantially cylindrical part which is closed off at its end side. A plurality of the openings 11, formed as slots which allow gas to be exchanged with internal regions, are provided at the periphery of the protective device 2. The protective device 2 has a coating 5 on the inside and on the outside. The coating is diagrammatically illustrated in the enlarged fragmentary view of FIG. 2B showing the portion IIB of FIG. 2A.

The coating 5 is provided on the inner and outer gas contact faces 4 of the protective device 2. The coating 5 has a layer thickness 7 in a range of from 10 μm to 50 μm. A proportion of pores 8 of the coating 5 per unit volume of the coating 5 is approximately 50%. The coating 5 has desiccant 6 for extracting water vapor from the gas flow, and noble metals 9 for catalytically converting pollutants in exhaust gas.

The gas probe proposed herein increases the operational reliability of exhaust systems of motor vehicles, in particular. The gas probe is also simple to produce within the context of series production.

We claim:

1. A gas probe, comprising:
   a sensitive sensor element configured to come into contact with a gas;
   at least one protective device at least regionally surrounding said sensitive sensor element, said at least one protective device including a gas contact face at least partially having a first hygroscopic surface; and
   a base body configured for coming into contact with the gas and at least partially having a second hygroscopic surface, said base body constituting a receptacle for said sensitive sensor element and said base body having an outer periphery with a thread for fixing the gas probe in a housing or in an exhaust system;
   said first hygroscopic surface and said second hygroscopic surface being formed at least partially with respective first and second hygroscopic coatings.

2. The gas probe according to claim 1, wherein said first hygroscopic coating or second hygroscopic coating includes a desiccant being resistant to high temperatures.

3. The gas probe according to claim 1, wherein said first hygroscopic coating or second hygroscopic coating has a layer thickness in a range of from 10 μm to 50 μm.

4. The gas probe according to claim 1, wherein said first hygroscopic coating or second hygroscopic coating has a porosity providing a pore volume per unit volume of said coating in a range of from 30% to 90%.

5. The gas probe according to claim 1, wherein said first hygroscopic coating or second hygroscopic coating includes an oxide.

6. The gas probe according to claim 5, wherein said oxide is at least one oxide selected from the group consisting of titanium oxide, zirconium oxide and aluminum oxide.

7. The gas probe according to claim 1, wherein said first hygroscopic coating or second hygroscopic coating includes constituents having a catalytic action.

8. The gas probe according to claim 7, wherein said constituents include a noble metal.

9. The gas probe according to claim 1, wherein said at least one protective device is a cap which includes a material resistant to high temperatures and can be deep-drawn.

10. The gas probe according to claim 1, wherein at least one of said at least one protective device or said base body is made from a material providing an oxide-forming surface.

11. The gas probe according to claim 1, wherein said at least one protective device is electrically heatable.

12. A lambda probe for analyzing exhaust gases of a mobile internal combustion engine, the lambda probe comprising:
   a sensitive sensor element configured to come into contact with the exhaust gases;
   at least one protective device at least regionally surrounding said sensitive sensor element, said at least one protective device including an exhaust gas contact face at least partially having a first hygroscopic surface; and
   a base body configured for coming into contact with the gas and at least partially having a second hygroscopic surface, said base body constituting a receptacle for said sensitive sensor element and said base having an outer periphery with a thread for fixing the lambda probe in a housing or in an exhaust system;
   said first hygroscopic surface and said second hygroscopic surface being formed at least partially with respective first and second hygroscopic coatings.

* * * * *